United States Patent [19]  
Chiang

[11] Patent Number: 4,545,313  
[45] Date of Patent: Oct. 8, 1985

[54] METHOD FOR MAKING A HAT  
[75] Inventor: Hsing-Hui Chiang, Taipei, Taiwan  
[73] Assignee: Asian Star, U.S.A., Inc., Galveston, Tex.  
[21] Appl. No.: 579,948  
[22] Filed: Feb. 14, 1984  
[51] Int. Cl.⁴ ............................................. D05B 23/00  
[52] U.S. Cl. ................................... 112/263.1; 2/192; 2/12; 2/199  
[58] Field of Search ............... 112/263.1; 2/DIG. 11, 2/196, 209.1, 192, 12, 186, 197, 199, 173; 223/7, 16, 12

[56] References Cited  
U.S. PATENT DOCUMENTS

| | | | |
|---|---|---|---|
| 1,404,616 | 1/1922 | Kronthal | 2/197 |
| 1,598,313 | 8/1926 | Rosenberg | 2/196 |
| 2,361,345 | 10/1944 | Young | 2/192 |
| 2,896,218 | 7/1959 | Lipschutz | 2/244 X |
| 3,184,757 | 5/1965 | Pennington | 2/199 |
| 4,179,753 | 12/1979 | Aronberg et al. | 2/DIG. 11 X |
| 4,268,918 | 5/1981 | Lee | 2/199 |
| 4,393,519 | 7/1983 | Nicastro | 2/DIG. 11 X |

Primary Examiner—Werner H. Schroeder  
Assistant Examiner—T. Graveline  
Attorney, Agent, or Firm—Vaden, Eickenroht, Thompson & Jamison

[57] ABSTRACT

The invention is a method for making a hat or visor with a three dimensional figure incorporated into the fabrication of the hat. The figure is sewn into the hat back and becomes integrated as part of the hat so that the figure is securely held erect above the bill of the hat.

2 Claims, 3 Drawing Figures

METHOD FOR MAKING A HAT

BACKGROUND OF THE INVENTION

The attachment of decorative figures such as animal heads to sun hats or visors has been by using adhesives. This type of adhesion can become loose with time and not provide a secure means for fastering the figure to the visor for active wear. There are other methods of attachment of the figures available such as staples, but none that incorporate the decorative figure sewn into the material of the visor or sun hat. The method of manufacture of this invention provides a safe and efficient manner of hat construction with a more durable product for active use that has a decorative figure as an attractive and interesting part of the hat.

BRIEF DESCRIPTION OF THE PRESENT INVENTION

The procedure for making the sun hat or visor includes sewing the various components together in such a fashion that the figure, which can be a decorative animal head or cartoon-type character is part of the finished product and not merely glued or stapled into Ilace on the hat. The hat back is provided with a facing of cloth or other suitable material which can be sewn directly to the figure. The figure can have a three dimensiorial appearance with protruding ears, nose and othrr facial features. The bottom of the figure is sewn to the hat band above the bill of the hat. The sides of the figure are left unsewn and padding or filling can be inserted between the front of the hat back and behind the figure for additional shape to the figure. The sides of the figure are then sewn to enclose the padding. The hat back is made of a sturdy material capable of holdirg the figure erect when the hat is worn.

This method of construction provides a durable sun hat or visor without using any glue or adbesives to hold the figure in place. This also eliminates the use of staples or other metal attachments which are not comfortable or safe for use on a hat.

BRIEF DESCRIPTION OF THE DRAWINGS

The accompanying drawings will more fully show the method of making the visor, in which.

DETAILED DESCRIPTION OF THE PREFERRED METHOD

The method of producing the sun hat or visor can be shown by reviewing the component parts and how each part is attached to form a fully completed hat. The method of attachment has been through sewing the fabric components together. The components can be made of any type of sewable material of suitable durability.

Figure 1:
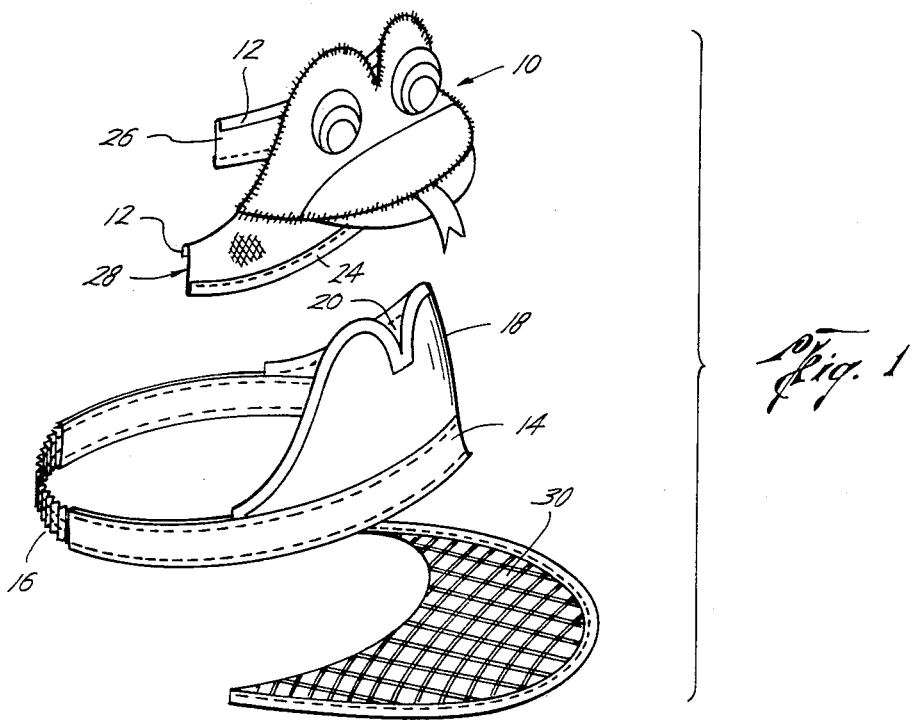
FIG. 1 is a view of the major component part of the hat prior to assembly.

The three dimensional figure is shown generally at 10(FIG. 1) and can be an animal head as shown or any other fanciful figure, cartoon-type character or head desired by the user. The figure can be made of any type of material desired to give the decorative result provided there is an edging of sewable material shown as fold 12 following the upper outline of the figure as shown in Fig. 1. The outline of the figure can be in any shape desired to express the animal or fanciful likeness.

Figure 3:
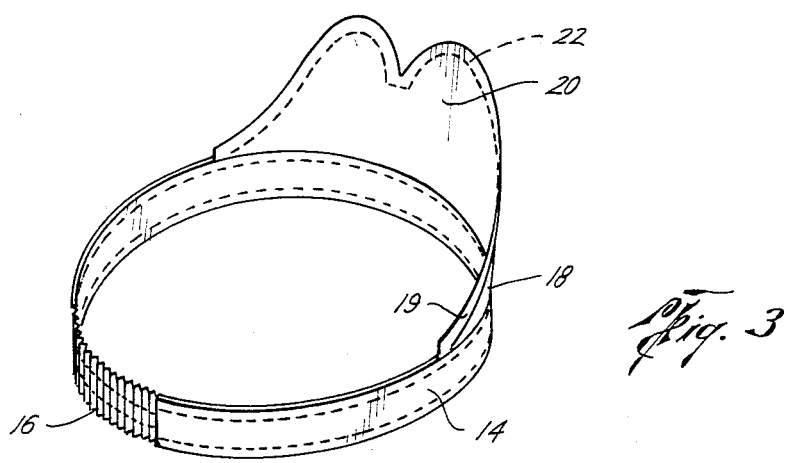
FIG. 3 is a view of the back of the hat back and facing prior to assembly

The hat band 14 is provided with an elastic insert 16 to accommodate varying head sizes. Extending from the band 14 on the front of the hat when worn is hat back 18. The material for the hat back 18 is sufficiently sturdy to hold its shape when upright. As shown more clearly in FIG. 3 a cloth facing 20 is firmly attached by seam 22 to hat back 18. Facing 20 extends from hat back 18 to an extent necessary to form a selvage 19 for sewing. Hat back 18 and the associated facing 20 have substantially the same upper outline as the FIG. 10 as can be seen in FIG. 1.

Figure 2:
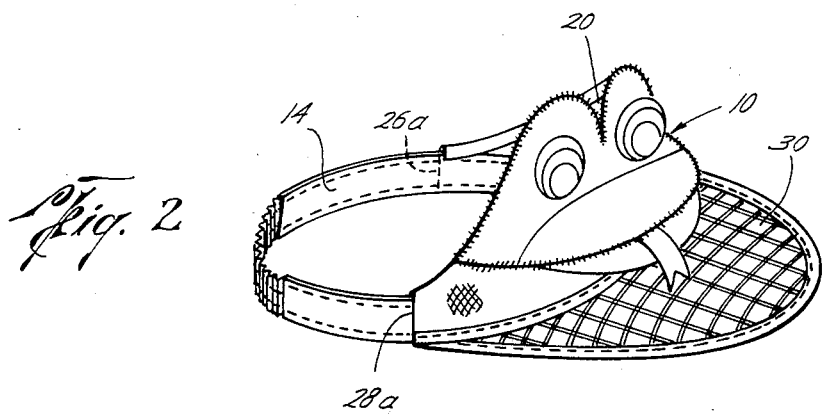
FIG. 2 is a view of the hat after assembly.

In constructing the visor or sun hat the FIG. 10 is fabricated to resemble the animal or face desired and is provided with fold 12 or similar means for sewing the upper outline of FIG. 10 to facing 20. The fold 12 is sewn to the part of facing 20 which extends from the hat back so that the seam line is in the selvage strip 19, along the hat back's upper edge. Hat back 18 provides support for FIG. 10 to hold the face erect on the front of the hat when the figure is sewn to facing 20 of hat back 18. The bottom edge 24 of the figure is sewn to the band 14. As shown in FIG. 1 the bottom edge 24 of the figure shows a binding strip for attachment which is optional. When the FIG. 10 is sewn to the facing 20 of hat back 18 sides 26 and 28 of the figure are not sewn to the hat back 18 or band 14. Padding or filling such as cotton (not shown) is inserted between the hat back 18 and the FIG. 10 to give additional shape and interest to the figure. After the desired amount of padding is added the sides 26 and 28 are seamed to the hat back 18 as shown in FIG. 2 at seams 26a and 28a.

Bill or brim 30 can be made of a plastic with thread webbing as shown or of another plastic or fabric suitable as a sturdy brim of a hat. Bill 30 is sewn to band 14 to complete the fabrication of the hat shown in the complete form in FIG. 2. This method of fabrication eliminates any glue or adhesives in the process of making a durable visor. Staples or mechanical attachments are eliminated. The finished product manufactured by this method has a neat appearance with the figure incorporated as an integral part of the visor.

What is claimed is:

1. A method for making a hat comprising the following steps:

Fabricating a band for encircling the head with an adjustable means for fitting a range of head sizes;..

Attaching to said band a hat back of sturdy material which extends upward from said band when the hat is worn said hat back having a cloth facing on the side of said hat back which is next to the head when worn and said facing extending from the back sufficiently to provide a selvage strip along the top edge and either side of said hat back:

Attaching a three dimensional figure to said hat back which figure has a fold on its outline of sewable material substantially corresponding to the selvage strip of the facing for attachment directly on said facing of said hat back;

Further attaching the lower part of said figure to said hat band leaving the sides open between the figure and said hat back:

Inserting padding material between said figure and said hat back through said open sides of said figure:

Sewing each of said sides of said figure to said band to enclose the padding material between said figure and said hat back and said band: and Affixing a hat bill to said band.

2. A method for making a hat comprising the following steps:

Fabricating a band for encircling the head:

Fabricating a three dimensional figure with an outline of sewable material;

Attaching to said band a hat back of sturdy fabric having upper and side outlines substantially corresponding to the outline of said figure;

Sewing the top of said three dimensional figure to the corresponding edges of said hat back;

Further attaching the lower part of said figure to said hat band leaving the sides of the figure open;

Inserting padding material between said figure and said hat back through said open sides of said figure;

Sewing the sides of said figure to said band to enclose the padding material; and Affixing a hat bill to said band.

* * * * *